United States Patent
Logunov

(10) Patent No.: US 6,392,753 B1
(45) Date of Patent: May 21, 2002

(54) ACCELERATED DAMAGE TESTING METHOD AND APPARATUS FOR LOW LOSS OPTICAL MATERIALS

(75) Inventor: Stephan L. Logunov, Corning, NY (US)

(73) Assignee: Corning Incorporated, Corning, NY (US)

(*) Notice: Subject to any disclaimer, the term of this patent is extended or adjusted under 35 U.S.C. 154(b) by 0 days.

(21) Appl. No.: 09/580,342

(22) Filed: May 25, 2000

(51) Int. Cl.⁷ ................................................. G01B 9/02
(52) U.S. Cl. ..................................................... 356/519
(58) Field of Search ................................ 356/432, 445, 356/451, 519; 250/337.12

(56) References Cited

U.S. PATENT DOCUMENTS

| | | | |
|---|---|---|---|
| 4,793,709 A | 12/1988 | Jabr et al. ................... | 356/445 |
| 5,943,136 A | 8/1999 | Pipino et al. ............... | 356/440 |
| 5,986,768 A | 11/1999 | Pipino ........................ | 356/440 |

FOREIGN PATENT DOCUMENTS

WO  WO 99/20996  4/1999

OTHER PUBLICATIONS

Scherer et al., "Cavity Ringdown Laser Absorption Spectroscopy: History, Development, and Application to Pulsed Molecular Beams," Chemical Review, 1997, pp. 25–51.

Richard Englen et al., "Cavity ring down spectroscopy on solid $C_{60}$," Journal of Chemical Physics, vol. 110, No. 5, Feb. 1999, pp. 2732–2733.

Pipino et al., "Evanescent wave cavity ring-down spectroscopy for probing for probing surface process" Chemical Physics Letters, vol. 208, Nov. 28, 1997, pp. 104–112.

*Primary Examiner*—Samuel A. Turner
(74) *Attorney, Agent, or Firm*—Adenike A. Adewuya; Timothy M. Schaeberle

(57) ABSTRACT

An accelerated radiation damage testing method for an optical sample includes disposing the optical sample inside or external to an optical cavity and injecting a predetermined number of light pulses into the optical cavity at a selected wavelength and at spaced intervals. Each light pulse injected into the optical cavity produces a train of pulses which are focused on the optical sample. The method further includes allowing each light pulse in the optical cavity to decay to a selected value and determining a change in a selected optical property of the optical sample after the optical sample has been exposed to a predetermined number of pulses.

18 Claims, 7 Drawing Sheets

US 6,392,753 B1

ACCELERATED DAMAGE TESTING METHOD AND APPARATUS FOR LOW LOSS OPTICAL MATERIALS

BACKGROUND OF THE INVENTION

1. Technical Field

The invention relates generally to methods and apparatus for measuring the effects of high-intensity, electromagnetic radiation, e. g., deep ultraviolet radiation, on the optical properties of an optical sample. More specifically, the invention relates to a method and an apparatus for conducting accelerated damage testing of an optical sample.

2. Background Art

One of the important consequences of exposing optical materials, including anti-reflection and high-reflection optical coatings, to high-intensity, electromagnetic radiation is possible degradation of their optical properties. For example, the response of high-purity, fused-silica glass to prolonged exposure to deep ultraviolet (UV) radiation such as 193 nm or 248 nm radiation is gradual monotonic development of absorption at the wavelength of the exposure beam. Increased absorption in the fused silica has an adverse effect on the transmission capabilities of the fused silica. Degradation of optical coatings exposed to deep UV radiation is also well known. Because optical materials (and optical coatings) can degrade over time under exposure to high-intensity, electromagnetic radiation, it is useful to be able to characterize the performance of the optical material under real-life conditions. Such characterization would be useful in determining the suitability of the optical material for a specific application and the useful life of the optical material.

The real-life performance of an optical sample under prolonged exposure to high-intensity, electromagnetic radiation can be estimated by applying doses of laser pulses to the optical sample and then measuring changes in a selected optical property (or properties) of the optical sample. Typically, the optical property of interest is absorption coefficient because it provides a direct measure of the transmission capabilities of the optical sample. For anti-reflective and high-reflective optical samples, the optical property of interest is typically reflectivity.

Currently, the damage testing requirements for a high-purity, fused-silica glass used in fabricating microlithography stepper and scanner lenses are specified as $10^{11}$ pulses of a 193 nm ArF excimer laser using an output energy intensity of 0.1 to 0.5 mJ/cm$^2$. At a pulse repetition rate of 400 Hz, it would take approximately eight years to test the glass at this low output energy intensity, which simulates the actual product dosage. It may be possible to fit the damage testing into a practical timeframe by increasing the repetition rate of the laser pulse. The repetition rate of a laser pulse is, however, limited by the capabilities of the laser. For example, the repetition rate of a commercially available ArF laser is currently limited to 400 Hz. Alternatively, the damage testing may be accelerated by using a laser having a higher output energy-intensity. It should noted, however, that the use of a higher output energy intensity may not produce glass behavior that is representative of the lower energy intensity that the product is exposed to in real-life operations. Damage thresholds can also be easily exceeded if the output energy-intensity of the laser pulse is too high. If damage thresholds are exceeded, extrapolation of the test results to real-life performance can be very misleading.

SUMMARY OF THE INVENTION

In one aspect, the invention relates to an accelerated radiation damage testing method for an optical sample which comprises disposing the optical sample inside an optical cavity so as to form an optically stable resonator. The method further includes injecting a predetermined number of light pulses into the optical cavity at a selected wavelength and at spaced intervals, allowing each light pulse injected into the optical cavity to decay to a selected value, and determining a change in an optical property of the optical sample after the optical sample has been exposed to the predetermined number of light pulses. In one embodiment, determining a change in an optical property of the optical sample includes monitoring the decay rate of the light pulse. In another embodiment, the optical sample is positioned substantially in the middle of the optical cavity. In another embodiment, a spatial length of each light pulse is much smaller than a length of the optical cavity.

In another aspect, the invention relates to an accelerated radiation damage testing method for an optical sample which comprises disposing the optical sample at an output end of an optical cavity. The method further includes injecting a predetermined number of light pulses into an input end of the optical cavity at a selected wavelength and at spaced intervals and allowing the light pulse in the optical cavity to decay to a selected value. A train of pulses is transmitted through the output end of the optical cavity and is focused on the optical sample. The method includes determining a change in an optical property of the optical sample after the optical sample has been exposed to a predetermined number of pulses.

In another aspect, the invention relates to an apparatus for conducting accelerated damage testing on an optical sample which comprises means for generating light pulses at a selected wavelength and at spaced intervals. The apparatus further includes an optically stable resonator for receiving the light pulses and producing a train of discrete pulses which are focused on the optical samples and means for monitoring the intensity of each light pulse.

DETAILED DESCRIPTION OF THE INVENTION

Figure 1:
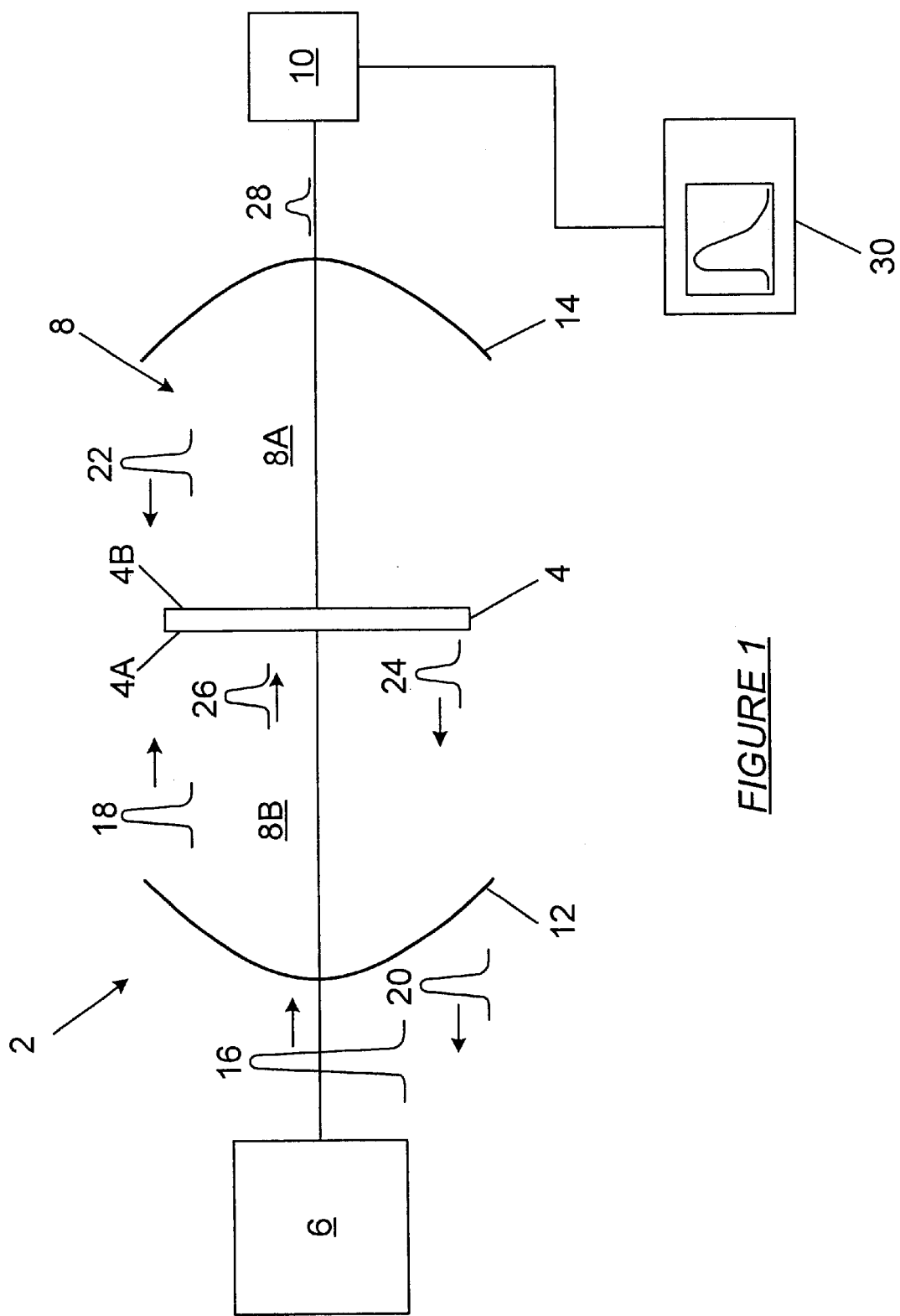
FIG. 1 illustrates a setup for conducting accelerated damage testing of an optical sample in accordance with one embodiment of the invention.

Embodiments of the invention provide a method and an apparatus for conducting accelerated damage testing of an optical sample. The optical sample could be a solid optical material or a thin film of coating. The embodiments of the invention take advantage of the multi-pass configuration used in "cavity ring-down spectroscopy" (CRDS) to increase the effective path length of the optical sample.

CRDS is a technique that is used to obtain absorption metrology of an absorbing medium. The CRDS technique was initially developed for mirror reflectivity measurements, but later was extended to quantitative absorption studies of gaseous species and condensed matter. See, for example, Scherer et al., "Cavity Ringdown Laser Absorption Spectroscopy: History, Development, and Application to Pulsed Molecular Beams," Chemical Review, 1997, pages 25–51, Richard Engeln et al., "Cavity ring down spectroscopy on solid $C_{60}$," Journal of Chemical Physics, Vol. 110, No. 5, February 1999, pages 2732–2733, U.S. Pat. No. 5,986,768 issued to Pipino, and U.S. Pat. No. 5,943,136 issued to Pipino et al.

A background discussion on CRDS is useful in fully understanding the invention. In CRDS, a single laser pulse is injected into an optical cavity that is formed from high-reflective mirrors. The laser pulse bounces back and forth within the optical cavity, with a small fraction of the laser pulse transmitting out of the optical cavity with each round trip. The intensity of the laser pulse within the optical cavity decays exponentially. The temporal decay of the laser pulse is determined by monitoring the intensity of the small fraction of light transmitted out of the optical cavity. The time required for the intensity of the transmitted light to decay to 1/e of its initial value is known as the "ring-down time" of the optical cavity. The ring-down time is a function of the length of the optical cavity, the round trip transit time of the laser pulse, and the magnitude of the intrinsic cavity losses. If an absorbing medium is disposed within the optical cavity, the absorbing medium absorbs a fraction of the laser pulse. Thus, the ring-down time is also a function of the absorption coefficient of the absorbing medium. By measuring the ring-down time of the optical cavity, the absorption coefficient of the absorbing medium within the optical cavity can be determined.

The accuracy with which the ring-down time is measured is highly sensitive to the intrinsic cavity losses. For gas phase measurements, the intrinsic cavity losses arise largely from the reflectivity of the mirrors. This is because the amount of light transmitted out of the optical cavity with each round trip of the laser pulse depends on the reflectivity of the mirrors. The higher the reflectivity of the mirrors, the less the amount of light transmitted out of the optical cavity, and the better the sensitivity of the system. The intrinsic cavity losses can, thus, be minimized by forming the optical cavity from highly reflective mirrors, e.g., mirrors having a reflectivity of approximately 0.9999 or better. Such mirrors are available for selected wavelengths using optical polishing techniques such as superpolishing. For a solid absorbing medium, Fresnel reflection losses from the surface of the solid introduce additional intrinsic cavity losses. Engeln et al. demonstrate that the additional intrinsic cavity losses can be minimized if the solid inside the optical cavity is a thin optically transparent substrate that together with the optical cavity defines various embedded cavities that are all optically stable. See, Richard Engeln et al., "Cavity ring down spectroscopy on solid $C_{60}$," supra. Pipino and Pipino et al., supra, describe alternate CRDS techniques that avoid placement of an absorbing material within a cavity.

Various exemplary embodiments of the invention will now be discussed in detail with reference to the accompanying figures. FIG. 1 illustrates a test setup 2 for conducting accelerated damage testing of an optical sample 4. The test setup 2 includes a laser source 6, an optical cavity 8, and a detector 10. The optical cavity 8 is formed from two concave reflective mirrors 12, 14. The accelerated damage testing is conducted by using the laser source 6 to direct a laser pulse 16 to the mirror 12 at a selected repetition rate. The optical sample 4 is placed inside the optical cavity 8, between the two reflective mirrors 12, 14. A portion 18 of the laser pulse 16 is injected into the optical cavity 8, while another portion 20 of the laser pulse 16 is reflected from the mirror 12. The power P of the laser pulse 18 injected into the optical cavity 8 is given by the following expression:

$$P = (1-R)P_0$$

where $P_0$ is the operating power of the laser source 6 and R is the reflectivity of the mirror 12. The operating power $P_0$ of the laser source 6 is selected such that the laser power P injected into the optical cavity 8 provides a desired power density at the location of the optical sample 4. For a given operating power $P_0$, equation (1) shows that there is a compromise between the reflectivity of the mirrors 12, 14 forming the optical cavity 8 and the amount of laser power that can be injected inside the optical cavity 8. The higher the reflectivity of the mirrors 12, 14, the less the power that can enter the optical cavity 8. Typically, the mirror reflectivity will be in a range from 0.98–0.9999.

The power density at the location of the optical sample 4 depends on the beam waist at the location of the optical sample 4 and the amount of laser power injected inside the optical cavity 8. The radius of curvature of the mirrors 12, 14 and the distance L between the mirrors 12, 14 are selected such that a desired beam waist is provided at the location of the optical sample 4. For a confocal resonator in which the radii of the concave mirrors 12, 14 are equal to the distance L between the mirrors 12, 14, the diameter of the beam waist $w_0$ formed in the middle of the optical cavity 8 is given by the following expression:

$$w_0 = \left(\frac{r\lambda}{\pi}\right)^{1/2} \quad (2)$$

where r is the radius of curvature of either one of the concave mirrors 12, 14, and $\lambda$ is the wavelength of the laser pulse injected into the optical cavity 8. Power density I is given by the following expression:

$$I = \frac{4P}{\pi w_0^2} \quad (3)$$

where P is the laser power injected inside the optical cavity 8. Thus, for example, if r is 3 m and $\lambda$ is 248 nm or 193 nm, $w_0$ will be approximately 0.4 mm. Assuming, for example, that the reflectivity of the mirrors 12, 14 is 0.99, and the starting laser power is 100 mJ per pulse, then 1 mJ can be injected inside the optical cavity 8. With a beam waist of 0.4 mm, a power density as high as 796 mJ/cm$^2$ can be reached at the location of the optical sample 4. Thus, advantageously, the laser source 6 can be run at a low power while achieving a high power density at the location of the optical sample 4.

The laser pulse 18 travels to the mirror 14 through the optical sample 4 and is reflected back toward the mirror 12. The laser pulse 22 represents the laser pulse 18 reflected from the mirror 14. The laser pulse 24 represents the laser pulse 18 reflected from the surface of the optical sample 4, and the laser pulse 26 represents the laser pulse 18 reflected from the mirror 12. The laser pulse 18 travels back and forth within the optical cavity 8. The length L of the optical cavity 8, i.e., the distance between the mirrors 12, 14, is selected to be much greater than the length of the pulses injected into the optical cavity 8 so that the pulses 18, 22 do not overlap at the location of the sample 4. Thus, the optical sample 4 sees a train of discrete pulses. The pulse length is equal to the pulse width of the laser source 6 multiplied by the speed of light ($3 \times 10^8$ m/s$^2$). The output pulses 28 transmitted through the mirror 14 are also discrete. The time separation $\Delta t$ between the output pulses 28 is given by the following expression:

$$\Delta t = \frac{2L}{c} \quad (4)$$

where L is the length of the optical cavity 8, i.e., the distance between the mirrors 12, 14, and c is the speed of light. Desired time separation between the output pulses 28 is obtained by adjusting the distance L between the mirrors 12, 14. The detector 10 detects and measures the intensity of the output pulse 28, and detected output pulse 28 is displayed on an oscilloscope 30.

Figure 2:
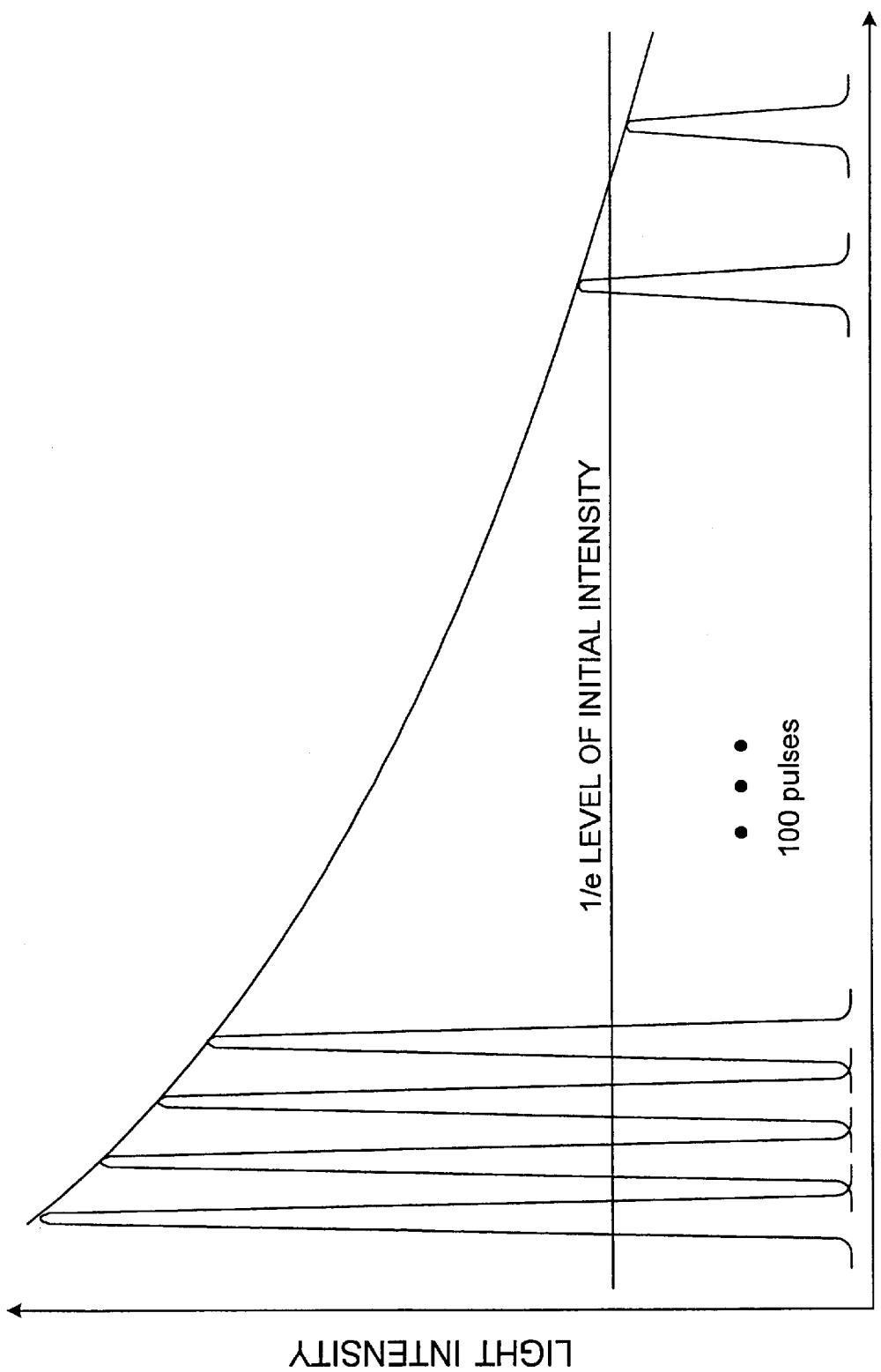
FIG. 2 shows a typical output of the optical cavity as a function of time.

FIG. 2 shows a typical exponential decay of the intensity of the output pulse 28. The ring-down time $\tau$ is given by the following expression:

$$\tau = \frac{L}{c(1-R)} \quad (5)$$

where L is the length of the optical cavity 8, c is the speed of light, and R is the reflectivity of the mirrors 12, 14. The ring-down time shown in equation (5) is for an empty optical cavity. If an absorbing medium, such as the optical sample 4, is disposed inside the optical cavity, the ring-down time will also be a function of the absorption coefficient of the absorbing medium. Thus, the absorption coefficient of the absorbing medium can be deduced from the ring-down time. It is important that the optical cavity 8 forms a stable resonator. If the optical cavity 8 does not form a stable resonator, the reflection loss from the surfaces of the optical sample 4 will result in substantial intrinsic cavity losses, which will diminish the absorption measurement sensitivity. For example, for most glass samples, the loss per reflection at normal incidence to the sample is 4–5%. The total reflection loss for each pass through the sample is about 8%. Because of the reflection loss, the laser pulse is significantly attenuated after each pass through the sample, making high-sensitivity absorption measurements nearly impossible. However, if every surface inside the optical cavity forms a matched cavity, then the incident radiation reflected at the surfaces of the optical sample 4 inside the optical cavity 8 will continue to resonate in the optical cavity 8.

The optical sample 4 is selected to be an optically transparent material so that the various embedded optical cavities are all matched. The various embedded optical cavities include the optical cavity 8, the optical cavities 8A, 8B, the optical cavity formed between the back surface 4B of the sample 4 and the mirror 12, and the optical cavity formed between the front surface 4A of the sample 4 and the mirror 14. When the embedded cavities are optically matched, the reflection loss is only about 0.04% per pulse pass as opposed to 8%. In addition, the optical sample 4 has a relatively short thickness (on the order of a few millimeters to a few centimeters) and is positioned substantially in the middle of the optical cavity 8 so that the portion of the laser pulse 18 that is first reflected from the mirror 12 and then reflected from the surface of the optical sample 4, e.g., laser pulse 26, overlaps with the portion of the laser pulse 18 that is transmitted through the optical sample 4 and then reflected from the mirror 14, e.g., laser pulse 24. The result is that reflection loss from the surface of the optical sample 4 does not contribute to attenuation of the intensity of the laser pulse 18, thus providing enhanced absorption measurement sensitivity.

In operation, the laser source 6 injects laser pulses into the optical cavity 8 at a selected wavelength and repetition rate. The reflectivity of the mirrors 12, 14, the length of the optical cavity 8, and the operating power of the laser source 6 are selected such that a desired power density is achieved at the location of the optical sample 4. Furthermore, the optical sample 4 is selected to be optically transparent and disposed within the optical cavity 8 so that the various embedded cavities are all optically matched. Each laser pulse injected into the optical cavity 8 is transmitted through the optical sample 4 many times as the intensity of the laser pulse decays. A portion of the laser pulse in the optical cavity 8 is transmitted through the mirror 14 with each round trip of the laser pulse and is detected by the detector 10. The ring-down time of the optical cavity 8 is determined for each laser pulse injected into the optical cavity 8. The laser pulse in the optical cavity is allowed to decay to 1/e of its original value, or lower than 1/e of its original value, before another pulse is injected into the cavity. The damage testing is complete when the optical sample 4 has been exposed to a desired number of pulses, as specified by the damage testing requirements. The change in the absorption coefficient of the optical sample 4 as a result of exposure to irradiation provides a measure of the extent of damage incurred in the optical sample 4, although other optical properties of the optical sample 4 may be measured before and after irradiation to determine the extent of damage incurred in the optical sample 4.

The invention described above provides advantages. In order to appreciate these advantages, it is useful to consider a specific example. Assume, for example, that the test setup 2 is to be used to conduct damage testing on a high-purity, fused-silica glass used in fabricating microlithography stepper and scanner lenses, and the damage testing requirements are specified as $10^{11}$ pulses of an 193 nm ArF excimer laser using an output energy intensity of 0.1 to 0.5 mJ/cm$^2$. Currently available excimer lasers have a pulse width of 10 ns. Thus, to achieve discrete pulses at the location of the optical sample, the length of the optical cavity 8 should be greater than 3 m. In this example, a cavity length of approximately 10 m is used, which is equivalent to 67 ns separation between pulses. Further, assume that the reflection and scattering at the surface of the glass (optical sample) are roughly 0.04% and that the reflectivity of the mirrors 12, 14 is approximately 0.99. It should be noted that ultra-low-loss optics is not currently available in the deep UV region, so the option of using a high-reflective mirror, e.g., having a reflectivity of 0.9999, is not available in this example.

To conduct the damage testing, laser pulses are injected into the optical cavity 8 using an ArF excimer laser. The operating power of the excimer laser is selected such that an initial power density of 0.5 mJ/cm$^2$ is achieved at the location of the sample. With these parameters, each laser pulse injected into the optical cavity 8 will traverse the optical cavity approximately 96 times before being attenuated to an intensity of 1/e times its original value (see FIG. 2). This means that a laser damage test equivalent to $10^{11}$ pulse exposure can be obtained with less than $10^9$ pulse exposure. If the sample is directly exposed to the excimer laser, and the excimer laser has a repetition rate of 400 Hz, it will take approximately eight years to apply $10^{11}$ pulses to the sample. However, with the test setup above, a laser damage test equivalent to $10^{11}$ pulses can be accomplished in about one month, a very significant reduction in testing time. This makes it possible to obtain the real-life performance of the sample within a practical timeframe. In addition, the reduction in testing time is achieved without exceeding the maximum specified power density at the location of the sample.

Figure 6:
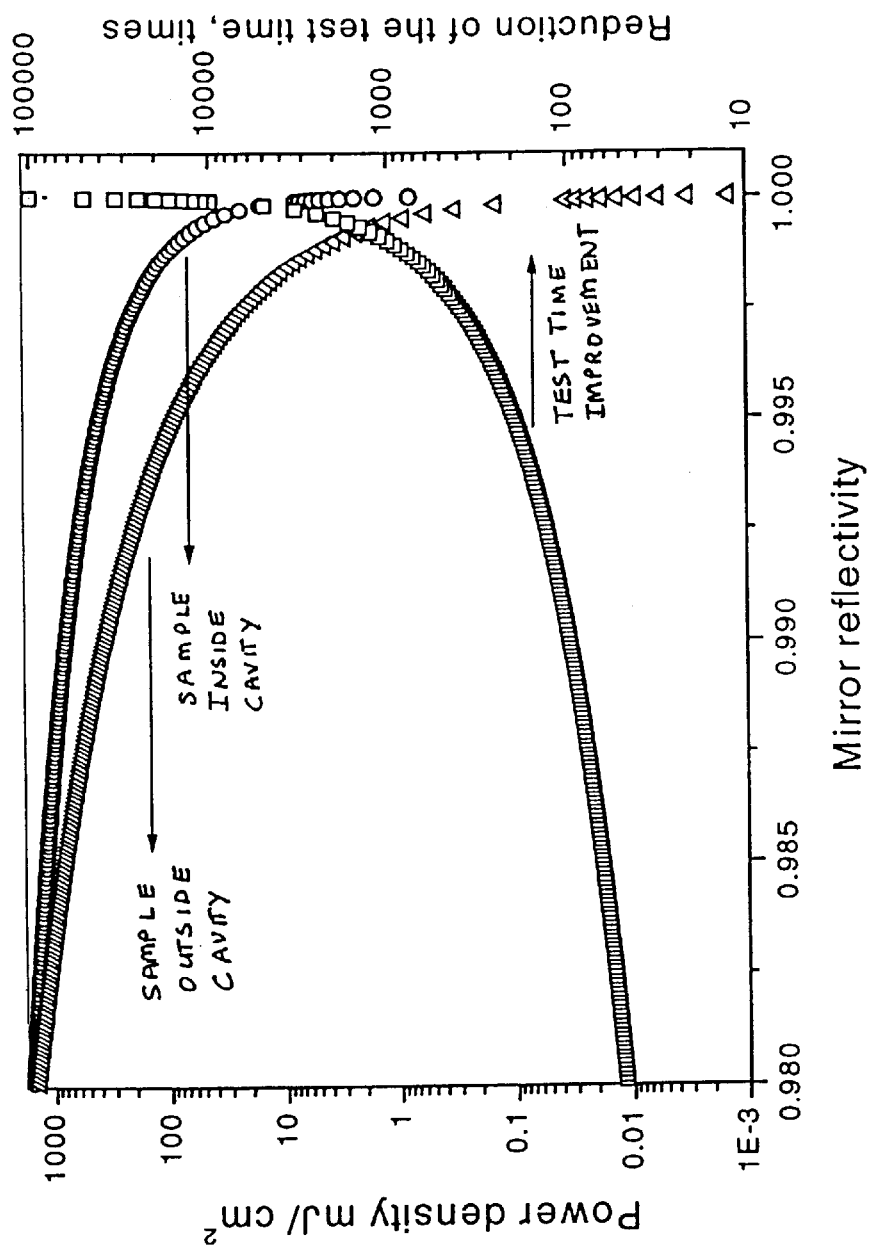
FIG. 6 illustrates a relationship between power density, damage testing time, and mirror reflectivity.

The reduction in damage testing time arises because each laser pulse produced by the laser source is transmitted through the sample many times. The ring-down time of the optical cavity can be synchronized with the pulse repetition rate of the laser source so that the damage testing process is continuous. There is, however, a tradeoff between the reduction in damage testing time that can be obtained with the test setup 2 and the maximum power density that can be achieved at the location of the sample 4. This is because the amount of laser power that can be injected into the optical cavity 8 and the ring-down time of the optical cavity 8 depend, at least in part, on the reflectivity of the mirrors 12, 14. In general, ring-down time increases as the reflectivity of the mirrors 12, 14 increases. The longer the ring-down time, the larger the number of times the laser pulse injected inside the optical cavity 8 passes through the optical sample 4. The amount of laser power that can be injected inside the optical cavity 8, however, decreases as the reflectivity of the mirrors 12, 14 increases. FIG. 6 illustrates a typical relationship between power density, damage testing time, and mirror reflectivity. For an initial laser pulse power of 100 mJ and a required power density of 100 mJ/cm² at the sample location, the optimal value for mirror reflectivity, for the example shown in FIG. 6, is 0.998.

Figure 3:
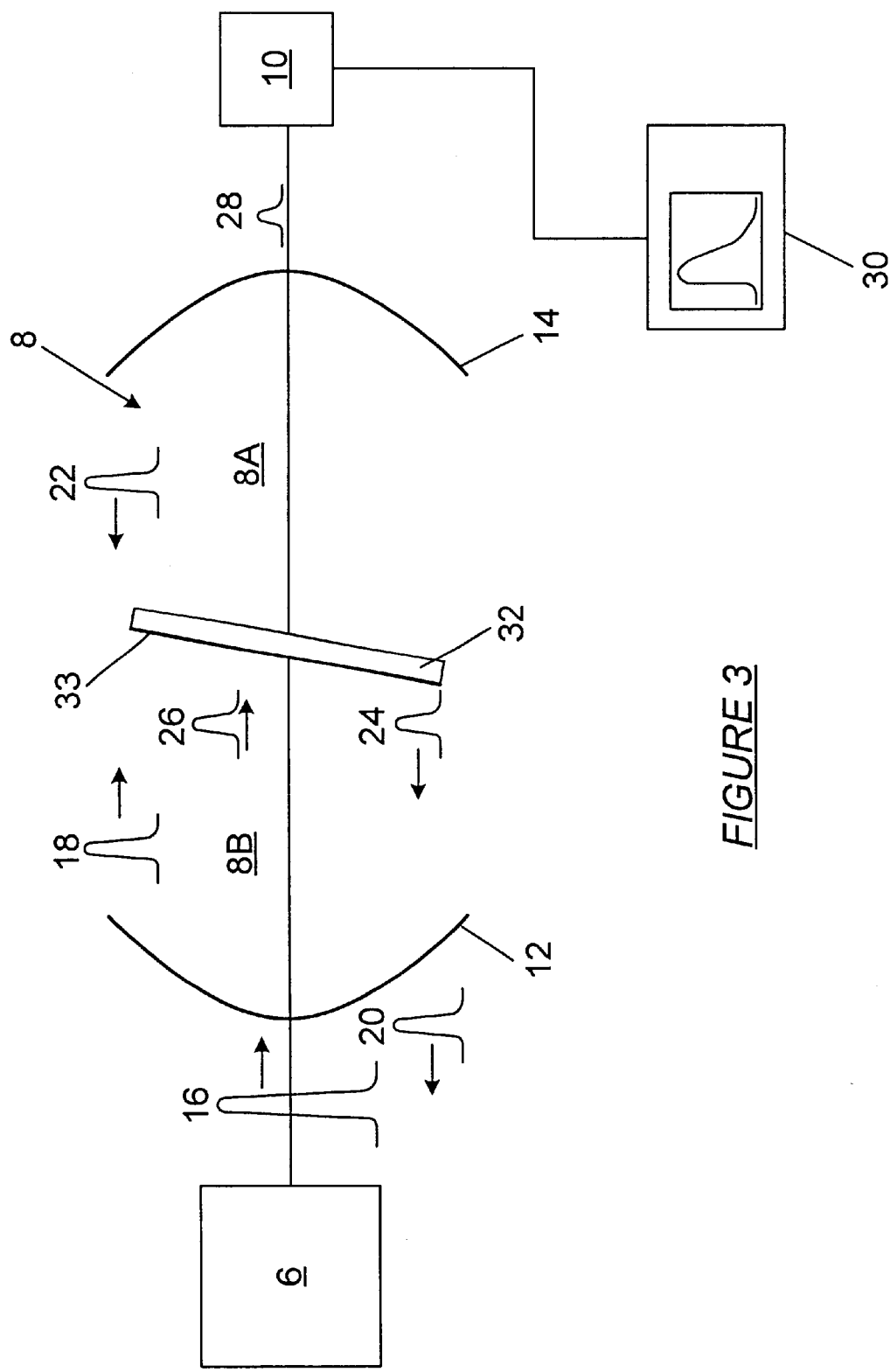
FIG. 3 illustrates a setup for conducting accelerated damage testing of an anti-reflective coating in accordance with another embodiment of the invention.

The acceleration damage testing method described above is also applicable to optical coatings. FIG. 3 illustrates a test setup 31 for accelerated damage testing of an anti-reflective coating. Except for the optical sample, the elements of the test setup 31 are the same as the elements of the test setup 2 (shown in FIG. 1). The optical sample in the test setup 31 includes a thin solid film of anti-reflective coating 33 applied on an optically transparent substrate 32. Thus, when the optical sample is placed inside the optical cavity 8, all the various embedded cavities are optically matched. It should be noted that the substrate 32 in the optical cavity 8 is intentionally slightly misaligned (approximately 0.1 degree) with respect to the vertical. This is to ensure that the laser pulses reflected from the mirrors 12, 14 do not get trapped within the cavities 8A, 8B. As in the test setup 2 shown in FIG. 1, the cavity ring-down time can be measured, and the changes in absorption coefficient of the anti-reflective coating 33 can be deduced from the ring-down time. Other techniques may also be used to determine the change in absorption coefficient and/or reflectivity of the anti-reflective coating 33.

Figure 4:
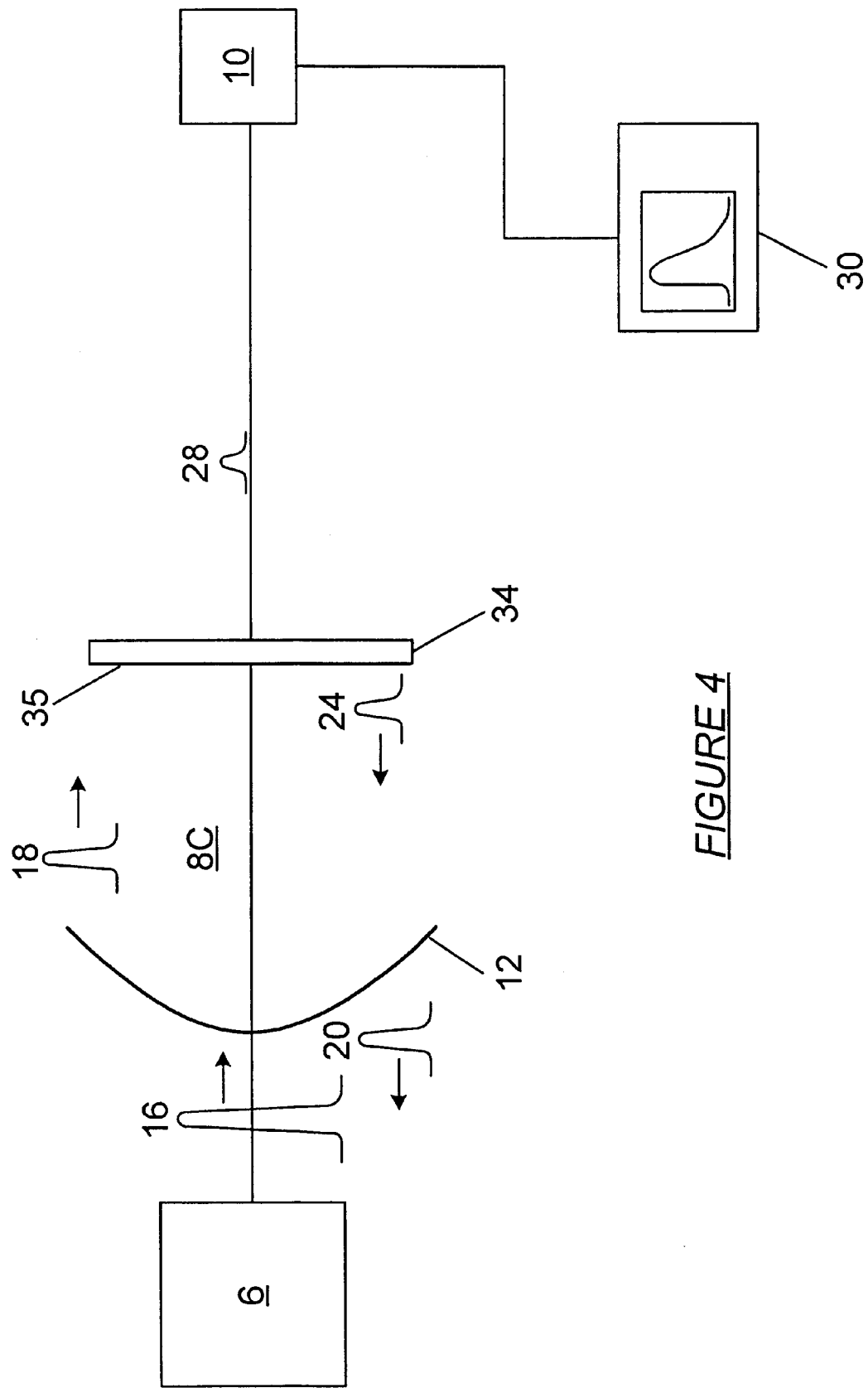
FIG. 4 illustrates a setup for conducting accelerated damage testing of a high-reflective coating in accordance with another embodiment of the invention.

FIG. 4 illustrates a test setup for accelerated damage testing of a high-reflective coating 35 applied on a substrate 34. In the test setup shown in FIG. 4, the substrate 34 with the high-reflective coating 35 replaces the mirror 14 (shown in FIG. 1) that would normally be positioned opposite the mirror 12. Thus, there is no solid object between the mirror 12 and the high-reflective coating 35, and the cavity ring-down time is a function of the reflectivity of the mirror 12, the reflectivity of the high-reflective coating 35, and the dimensions of the optical cavity 8C. It should be noted that unlike the test setup 2 shown in FIG. 1, reflection losses which occur as a result of placing a solid sample inside an optical cavity is not a concern. The change in the reflectivity of the high-reflective coating 35 may be deduced from the cavity ring-down time, for example, using equation (5) above. The change in reflectivity of the high-reflective coating 35 will provide a measure of the extent of damage incurred in the high-reflective coating 35 as a result of exposure to the laser energy.

Figure 5A:
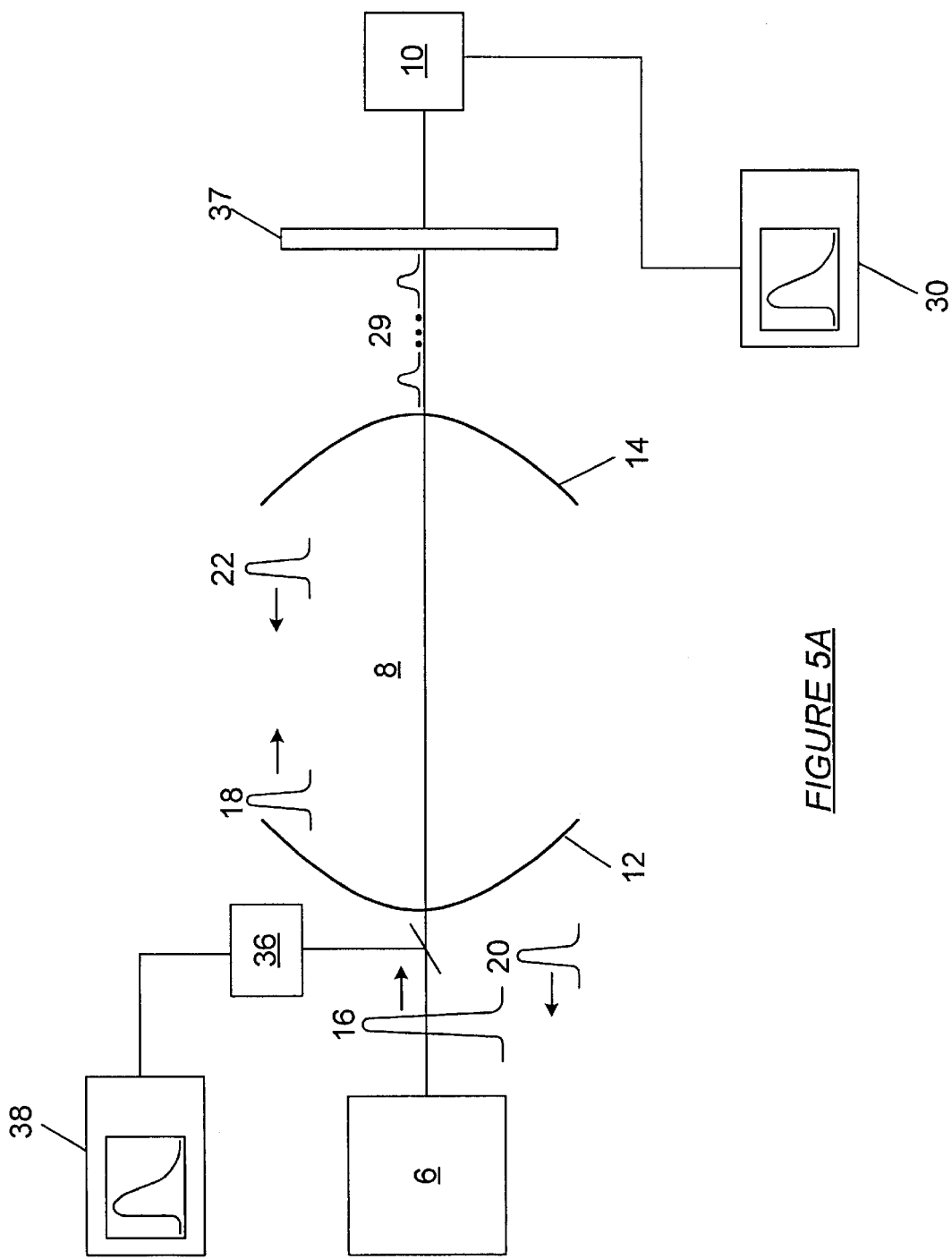
FIGS. 5A and 5B illustrate setups for conducting accelerated damage testing of an optical sample disposed external to an optical cavity in accordance with another embodiment of the invention.
Figure 5B:
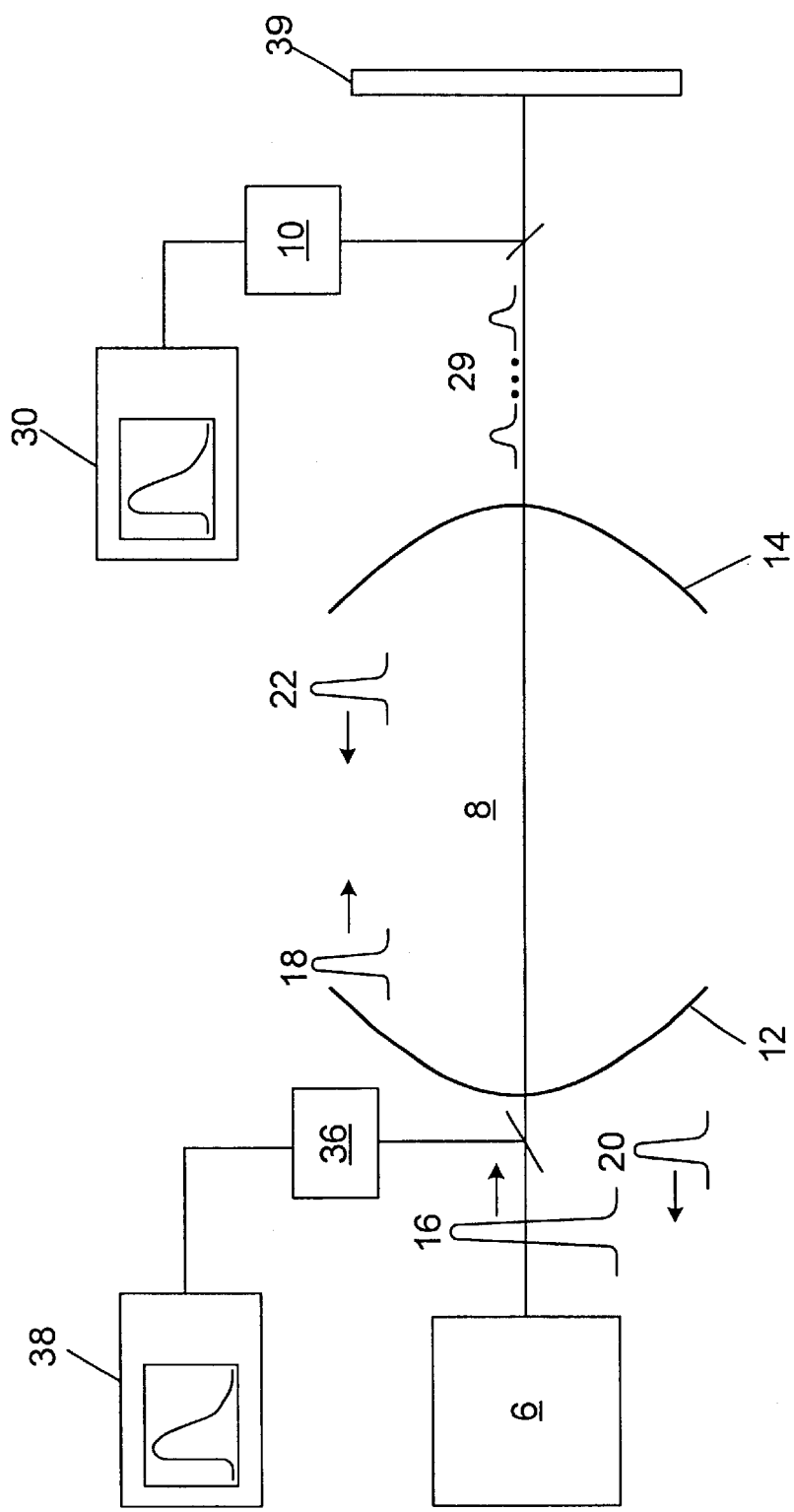

The test setups described in FIGS. 1 and 3 place an optical sample inside an optical cavity. FIGS. 5A and 5B show test setups in which optical samples 37, 39 are disposed external to the optical cavity 8. In FIG. 5A, the optical sample 37 is either an optically transparent material or an optically transparent substrate which has an anti-reflective coating applied on its surface. The detector 10 detects the portion of the output pulses 29 that is transmitted through the optical sample 37 while the detector 36 detects the portion of the output pulse 16. The pulses detected by the detectors 10 and 36, respectively, are displayed on the oscilloscopes 30 and 38, respectively. The change in intensity of the pulses detected by the detectors 10 and 36 are used to deduce the change in absorption, or transmission loss, of the optical sample 37. In FIG. 5B, the optical sample 39 is a substrate which has a high-reflective sample applied on its surface. In this case, the detector 36 detects the pulses 16 exiting the laser source 6 and the detector 36 detects the portion of the pulse 28 that is reflected from the optical sample 39.

The empty optical cavity 8 shown in FIGS. 5A and 5B splits a single laser pulse into a train of pulses 29, which can be focused on the optical sample to reach the desired power density. It should be noted that in order to obtain the train of pulses, the spatial length of the laser pulse injected into the optical cavity must be much less than the length of the optical cavity. This approach allows the time needed to expose a sample to a given number of pulses to be reduced by nearly two orders of magnitude compared to direct exposure of the sample at a selected laser pulse repetition rate. Desired power density at the location of the optical sample 37,39 can be obtained by focusing the output of the optical cavity 8 on the optical sample. The diameter of the beam waist $d_s$ at the focus of the mirrors 12, 14 can be expressed as:

$$d_s = 2.44 \frac{f\lambda}{D} \tag{5}$$

where f is the focus length of the mirrors, $\lambda$ is the wavelength of light, and D is the diameter of the incident beam. Suppose that the focus length of the mirrors is 15 cm, the wavelength of the laser beam is 200 nm, and the diameter of the incident beam is 1 cm, then the beam waist at the sample location will be 60 $\mu$m. As shown in FIG. 6, for mirrors with reflectivity of 0.99, a power density as high as approximately 350 mJ/cm² can be obtained at the sample location, when the sample is placed outside the optical cavity.

The invention described uses the multi-pass configuration of CRDS to increase the effective path length of the optical sample to be tested. However, it should be clear that there are several key differences between the method and apparatus described above and CRDS. As previously mentioned, the primary objective of CRDS is to obtain the absorption metrology of an optical sample, not to damage the optical sample. In particular, only a single laser pulse is used with just enough energy to be detected. The embodiments described above, however, use many pulses with sufficient power to simulate prolonged irradiation. Tradeoff is made between mirror reflectivity and laser power to allow sufficient power to be injected inside the optical cavity. Because the primary objective is not to measure absorption, ordinary optics, i.e., mirrors having reflectivity of 0.99, can be used in the construction of the optical cavity. This allows damage testing to be conducted in the short-wavelength region, which is where high-purity, fused-silica glass, for example, exhibits the monotonically increasing absorption pattern.

While the invention has been described with respect to a limited number of embodiments, those skilled in the art, having the benefit of this disclosure, will appreciate numerous modifications and variations therefrom. It is intended that the appended claims cover all such modifications and variations as fall within the true spirit and scope of the invention.

What is claimed is:

1. An accelerated radiation damage testing method for an optical sample, comprising:

disposing the optical sample inside an optical cavity so as to form an optically stable resonator;

injecting a plurality of light pulses into the optical cavity at a selected wavelength and at spaced intervals;

adjusting a length of the optical cavity such that the optical sample is exposed to a train of non-overlapping pulses;

allowing each light pulse injected into the optical cavity to decay to a selected value; and determining a change in a selected optical property of the optical sample after the optical sample has been exposed to a predetermined number of light pulses.

2. The method of claim 1, wherein determining a change in a selected optical property of the sample includes monitoring the decay rate of the light pulse.

3. The method of claim 1, wherein the selected optical property of the optical sample is absorption coefficient.

4. The method of claim 1, wherein the optical sample is positioned substantially in the middle of the optical cavity.

5. The method of claim 1, wherein a spatial length of each light pulse is much smaller than the length of the optical cavity.

6. The method of claim 1, wherein the optical sample includes an anti-reflective coating applied on the surface of an optically transparent substrate.

7. An accelerated radiation damage testing method for a high-reflective coating, comprising:

applying a thin film of the high-reflective coating on a substrate;

arranging a mirror and the substrate in an opposing and spaced relation so as to define an optical cavity;

injecting a predetermined number of light pulses into the optical cavity at a selected wavelength and at spaced intervals;

allowing each light pulse injected into the optical cavity to decay to a selected value; and determining a change in a selected optical property of the high-reflective coating after the predetermined number of light pulses have been injected into the optical cavity.

8. The method of claim 7, wherein the selected optical property of the high-reflective coating is reflectivity.

9. An accelerated radiation damage testing method for an optical sample, comprising:

disposing the optical sample at an output end of an optical cavity;

injecting a predetermined number of light pulses into an input end of the optical cavity at a selected wavelength and at spaced intervals;

allowing the light pulse in the optical cavity to decay to a selected value, wherein a train of pulses is transmitted through the output end of the optical cavity and is focused on the optical sample; and determining a change in a selected optical property of the optical sample after the optical sample has been exposed to a predetermined number of the train of pulses.

10. The method of claim 9, wherein determining a change in an optical property of the sample includes monitoring attenuation of the train of pulses.

11. The method of claim 9, wherein the selected optical property of the sample is absorption coefficient.

12. The method of claim 9, wherein the optical sample includes an anti-reflective coating applied on the surface of an optically transparent substrate.

13. The method of claim 12, wherein the optical property of the optical sample is reflectivity.

14. The method of claim 1, wherein each light pulse has a wavelength below 400 nm.

15. An accelerated radiation damage testing method for an optical sample, comprising:

disposing the optical sample inside an optical cavity so as to form an optically stable resonator;

injecting a plurality of light pulses into the optical cavity at spaced intervals, each light pulse having a wavelength below 400 nm;

adjusting a length of the optical cavity such that the optical sample is exposed to a train of non-overlapping pulses.

allowing each light pulse injected into the optical cavity to decay to a selected value; and determining a change in a selected optical property of the optical sample after the optical sample has been exposed to a predetermined number of light pulses.

16. The method of claim 15, wherein disposing the optical sample inside the optical cavity comprises positioning the optical sample substantially in the middle of the optical cavity.

17. The method of claim 15, wherein the length of the optical cavity is greater than 1 m.

18. The method of claim 15, wherein the length of the optical cavity ranges from 3 m to 10 m.

* * * * *